United States Patent
Argiro et al.

(10) Patent No.: US 7,031,504 B1
(45) Date of Patent: Apr. 18, 2006

(54) IMAGE DATA BASED RETROSPECTIVE TEMPORAL SELECTION OF MEDICAL IMAGES

(75) Inventors: Vincent J. Argiro, Minneapolis, MN (US); Marek Brejl, Plymouth, MN (US); Renee Maheshwari Rashid, Santa Clara, CA (US); Todd Johnson, Minneapolis, MN (US); Milan Brejl, Rozmov pod Radhostem (CZ)

(73) Assignee: Vital Images, Inc., Minnetonka, MN (US)

( * ) Notice: Subject to any disclaimer, the term of this patent is extended or adjusted under 35 U.S.C. 154(b) by 701 days.

(21) Appl. No.: 09/669,395

(22) Filed: Sep. 26, 2000

(51) Int. Cl.
*G06K 9/00* (2006.01)
*G06K 9/34* (2006.01)

(52) U.S. Cl. ...................... 382/131; 382/173
(58) Field of Classification Search ............... 382/282, 382/131, 132, 209, 219–221, 274, 264, 173, 382/128–134; 600/479, 481, 513
See application file for complete search history.

(56) References Cited

U.S. PATENT DOCUMENTS

| | | | | |
|---|---|---|---|---|
| 4,547,892 A | * | 10/1985 | Richey et al. | 378/8 |
| 4,788,975 A | * | 12/1988 | Shturman et al. | 606/7 |
| 5,133,020 A | * | 7/1992 | Giger et al. | 382/128 |
| 5,533,085 A | | 7/1996 | Sheehan et al. | 378/95 |
| 5,570,430 A | * | 10/1996 | Sheehan et al. | 382/128 |
| 5,781,010 A | * | 7/1998 | Kawasaki et al. | 324/309 |
| 5,910,111 A | * | 6/1999 | Hunziker | 600/407 |
| 6,154,516 A | * | 11/2000 | Heuscher et al. | 378/15 |
| 6,393,091 B1 | * | 5/2002 | Slack et al. | 378/8 |
| 6,510,337 B1 | * | 1/2003 | Heuscher et al. | 600/428 |
| 6,563,941 B1 | * | 5/2003 | O'Donnell et al. | 382/131 |
| 2002/0165448 A1 | * | 11/2002 | Ben-Haim et al. | 600/424 |

FOREIGN PATENT DOCUMENTS

EP  1088517  4/2001

OTHER PUBLICATIONS

Clos et al., "A Novel Algorithm for Classification of SPECT images of a Human Heart" 1996, IEEE, 1-5.*
Belohlavek et al. "Multidimensional Ultrasonic Visualization in Cardiology," 1992, IEEE, 1137-1145.*
Sonka, M., et al., "5.2.5 Border detection as dynamic programming", *Image Processing, Analysis, and Machine Vision, Second Edition*, 158-163, (1999).
Veldhuis, R., "Restoration of Lost Samples in Digital Signals", *Prentice Hall International Series in Acoustics, Speech and Signal Processing*, 28-57, (Apr. 26, 1993).

* cited by examiner

*Primary Examiner*—Joseph Mancuso
*Assistant Examiner*—Shefali Patel
(74) *Attorney, Agent, or Firm*—Schwegman, Lundberg, Woessner & Kluth, P.A.

(57) ABSTRACT

Systems and methods for deriving a cardiac cycle signal by selecting images of a portion of a cardiovascular system include receiving a plurality of images from a scanner that have been recorded over a period of time. The images represent one or more locations along the extent of the cardiovascular system. The images are then selected based on common criteria determined from the plurality of images and without reference to an external signal. The common criteria comprises changes in the size of a cross section of the aorta, changes in the volume of the heart, changes in the area of a cross section of the heart. In addition, the criteria can include the mean pixel difference between adjacent images.

26 Claims, 5 Drawing Sheets

IMAGE DATA BASED RETROSPECTIVE TEMPORAL SELECTION OF MEDICAL IMAGES

FIELD

The present invention relates generally to medical imaging, and more particularly to systems and methods for performing temporal selection of medical images based on image data.

COPYRIGHT NOTICE/PERMISSION

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the software and data as described below and in the drawings hereto: Copyright © 2000, Vital Images, Inc. All Rights Reserved.

BACKGROUND

Heart disease is a significant public health problem. Therefore, in medicine, it is of considerable value to obtain cross-sectional and volumetric images of the human heart. Applications include angiography of coronary vessels for detecting stenosis, examination of the thoracic aorta for dissection of the vessel wall, and quantization of calcium deposits in the coronary arteries as a marker for atheroscerotic plaque.

Recently, this last application has gathered significant interest due to the finding that the exam can be performed with a conventional high-speed helical CT (Computer Tomography) scanner, as opposed to the more expensive and less prevalent electron beam CT scanner. However, helical CT scanners are still too slow to "freeze" the motion of the heart, resulting in some cross-sectional images being blurred and out of register with other images captured at a different phase of the heart's cycle of contraction (systole) and relaxation (diastole).

As a consequence, methods have been introduced to determine the heart cycle phase of axial CT images by simultaneously recording the electrocardiogram (EKG), and synchronizing this signal with the sequence of images. Since the high amplitude "r-wave" of the EKG is a reliable and very brief indicator of the onset of ventricular contraction, it is straightforward to use its peak as an indicator of when heart motion will be near its most violent. It is then possible to either shut down image acquisition during these times, or retrospectively eliminate images that have been acquired at these times. This method is called EKG gating.

The disadvantage of EKG gating is that it significantly lengthens the exam time due to the need to wire the patient with electrodes, etc. It also introduces additional complications in the design of the CT scanner and of the software used to post-process the acquired images. It may additionally require manual verification of the selection of images, and introduces the possibility of mismatching EKG traces and images from different patients.

As a result, there is a need in the art for systems and methods that can filter images acquired during an image scan of a patient without the need for external monitoring devices such as EKG monitors.

SUMMARY

The above-mentioned shortcomings, disadvantages and problems are addressed by the present invention, which will be understood by reading and studying the following specification.

In one embodiment of the invention, a method for selecting images of a portion of a cardiovascular system includes receiving a plurality of images from a scanner that have been recorded over a period of time. The images represent one or more locations along the extent of the cardiovascular system. The images are then selected based on common criteria determined from the plurality of images and without reference to an external signal.

In some embodiments, the common criteria comprises changes in the size of a cross section of the aorta. In alternative embodiments, the common criteria comprises changes in the volume of the heart. In still further embodiments, the common criteria comprises changes in the area of a cross section of the heart. In yet other embodiments, the criteria includes the mean pixel difference between adjacent images.

The present invention describes systems, clients, servers, methods, and computer-readable media of varying scope. In addition to the aspects and advantages of the present invention described in this summary, further aspects and advantages of the invention will become apparent by reference to the drawings and by reading the detailed description that follows.

DETAILED DESCRIPTION

In the following detailed description of exemplary embodiments of the invention, reference is made to the accompanying drawings which form a part hereof, and in which is shown by way of illustration specific exemplary embodiments in which the invention may be practiced. These embodiments are described in sufficient detail to enable those skilled in the art to practice the invention, and it is to be understood that other embodiments may be utilized and that logical, mechanical, electrical and other changes may be made without departing from the scope of the present invention. The following detailed description is, therefore, not to be taken in a limiting sense.

In the Figures, the same reference number is used throughout to refer to an identical component which appears in multiple Figures. Signals and connections may be referred to by the same reference number or label, and the actual meaning will be clear from its use in the context of the description.

The detailed description is divided into multiple sections. In the first section the hardware and operating environment of different embodiments of the invention is described. In the second section, the software environment of varying embodiments of the invention is described. In the third section, methods of various embodiments of the invention are described. In the final section, a conclusion is provided.

Hardware and Operating Environment

Figure 1:
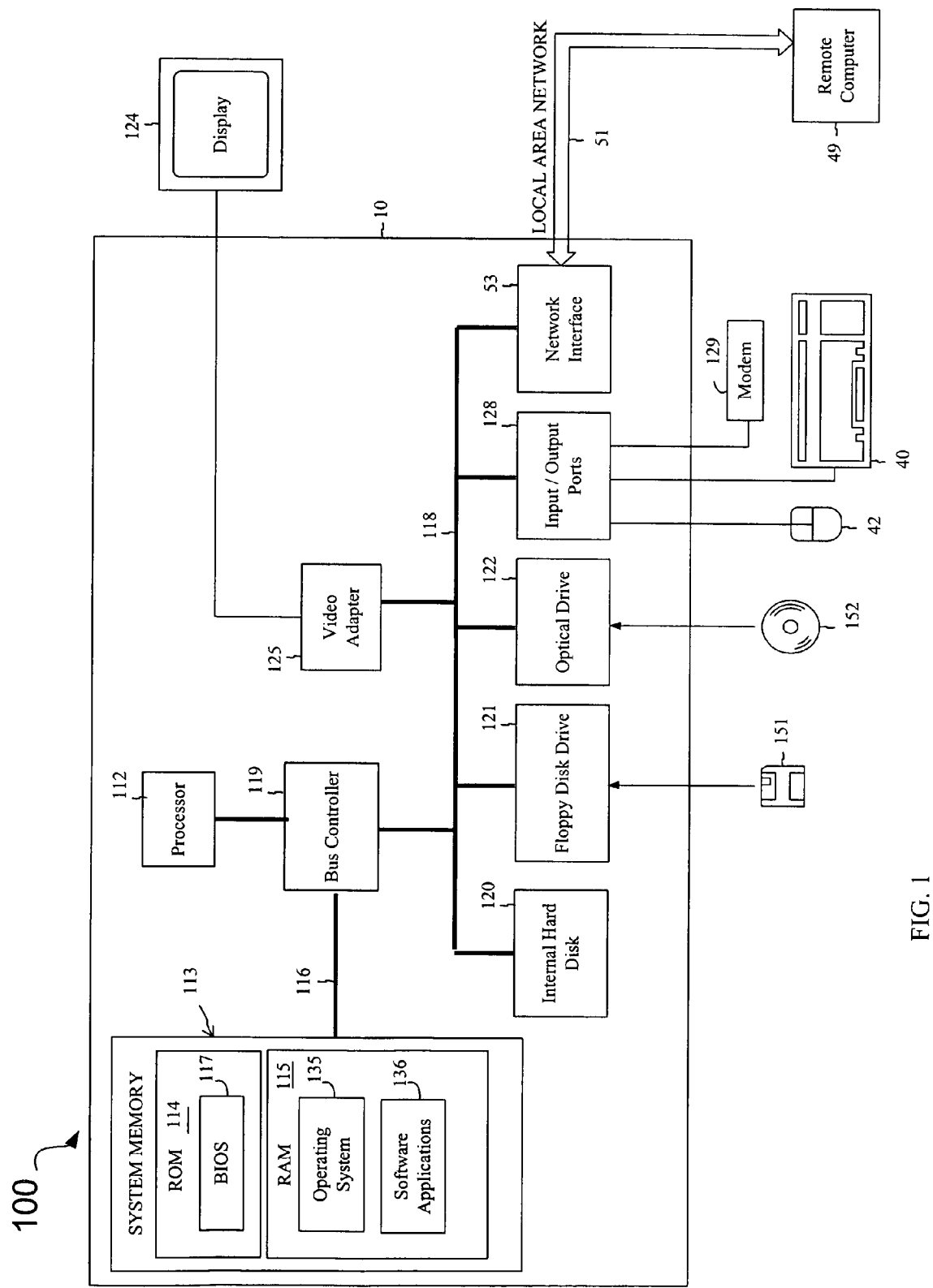
FIG. 1 is a block diagram of the hardware and operating environment in which different embodiments of the invention can be practiced.

FIG. 1 is a diagram of the hardware and operating environment in conjunction with which embodiments of the invention may be practiced. The description of FIG. 1 is intended to provide a brief, general description of suitable computer hardware and a suitable computing environment in conjunction with which the invention may be implemented. Although not required, the invention is described in the general context of computer-executable instructions, such as program modules, being executed by a computer, such as a personal computer, workstation, or a server computer. Generally, program modules include routines, programs, objects, components, data structures, etc., that perform particular tasks or implement particular abstract data types.

Moreover, those skilled in the art will appreciate that the invention may be practiced with other computer system configurations, including hand-held devices, multiprocessor systems, microprocessor-based or programmable consumer electronics, network PCs, minicomputers, mainframe computers, and the like. The invention may also be practiced in distributed computing environments where tasks are performed by remote processing devices that are linked through a communications network. In a distributed computing environment, program modules may be located in both local and remote memory storage devices.

As shown in FIG. 1, the computing system 100 includes a processor. The invention can be implemented on computers based upon microprocessors such as the PENTIUM® family of microprocessors manufactured by the Intel Corporation, the MIPS® family of microprocessors from the Silicon Graphics Corporation, the POWERPC® family of microprocessors from both the Motorola Corporation and the IBM Corporation, the PRECISION ARCHITECTURE® family of microprocessors from the Hewlett-Packard Company, the SPARC® family of microprocessors from the Sun Microsystems Corporation, or the ALPHA® family of microprocessors from the Compaq Computer Corporation. Computing system 100 represents any personal computer, laptop, server, or even a battery-powered, pocket-sized, mobile computer known as a hand-held PC.

The computing system 100 includes system memory 113 (including read-only memory (ROM) 114 and random access memory (RAM) 115), which is connected to the processor 112 by a system data/address bus 116. ROM 114 represents any device that is primarily read-only including electrically erasable programmable read-only memory (EEPROM), flash memory, etc. RAM 115 represents any random access memory such as Synchronous Dynamic Random Access Memory.

Within the computing system 100, input/output bus 118 is connected to the data/address bus 116 via bus controller 119. In one embodiment, input/output bus 118 is implemented as a standard Peripheral Component Interconnect (PCI) bus. The bus controller 119 examines all signals from the processor 112 to route the signals to the appropriate bus. Signals between the processor 112 and the system memory 113 are merely passed through the bus controller 119. However, signals from the processor 112 intended for devices other than system memory 113 are routed onto the input/output bus 118.

Various devices are connected to the input/output bus 118 including hard disk drive 120, floppy drive 121 that is used to read floppy disk 151, and optical drive 122, such as a CD-ROM drive that is used to read an optical disk 152. The video display 124 or other kind of display device is connected to the input/output bus 118 via a video adapter 125.

A user enters commands and information into the computing system 100 by using a keyboard 40 and/or pointing device, such as a mouse 42, which are connected to bus 118 via input/output ports 128. Other types of pointing devices (not shown in FIG. 1) include track pads, track balls, joy sticks, data gloves, head trackers, and other devices suitable for positioning a cursor on the video display 124.

As shown in FIG. 1, the computing system 100 also includes a modem 129. Although illustrated in FIG. 1 as external to the computing system 100, those of ordinary skill in the art will quickly recognize that the modem 129 may also be internal to the computing system 100. The modem 129 is typically used to communicate over wide area networks (not shown), such as the global Internet. The computing system may also contain a network interface card 53, as is known in the art, for communication over a network.

Software applications 136 and data are typically stored via one of the memory storage devices, which may include the hard disk 120, floppy disk 151, CD-ROM 152 and are copied to RAM 115 for execution. In one embodiment, however, software applications 136 are stored in ROM 114 and are copied to RAM 115 for execution or are executed directly from ROM 114.

In general, the operating system 135 executes software applications 136 and carries out instructions issued by the user. For example, when the user wants to load a software application 136, the operating system 135 interprets the instruction and causes the processor 112 to load software application 136 into RAM 115 from either the hard disk 120 or the optical disk 152. Once software application 136 is loaded into the RAM 115, it can be used by the processor 112. In case of large software applications 136, processor 112 loads various portions of program modules into RAM 115 as needed.

The Basic Input/Output System (BIOS) 117 for the computing system 100 is stored in ROM 114 and is loaded into RAM 115 upon booting. Those skilled in the art will recognize that the BIOS 117 is a set of basic executable routines that have conventionally helped to transfer information between the computing resources within the computing system 100. These low-level service routines are used by operating system 135 or other software applications 136.

In one embodiment computing system 100 includes a registry (not shown) which is a system database that holds configuration information for computing system 100. For example, Windows® 95, Windows® 98®, Windows® NT, and Windows 2000® by Microsoft maintain the registry in two hidden files, called USER.DAT and SYSTEM.DAT, located on a permanent storage device such as an internal disk.

Software Environment

Figure 2:
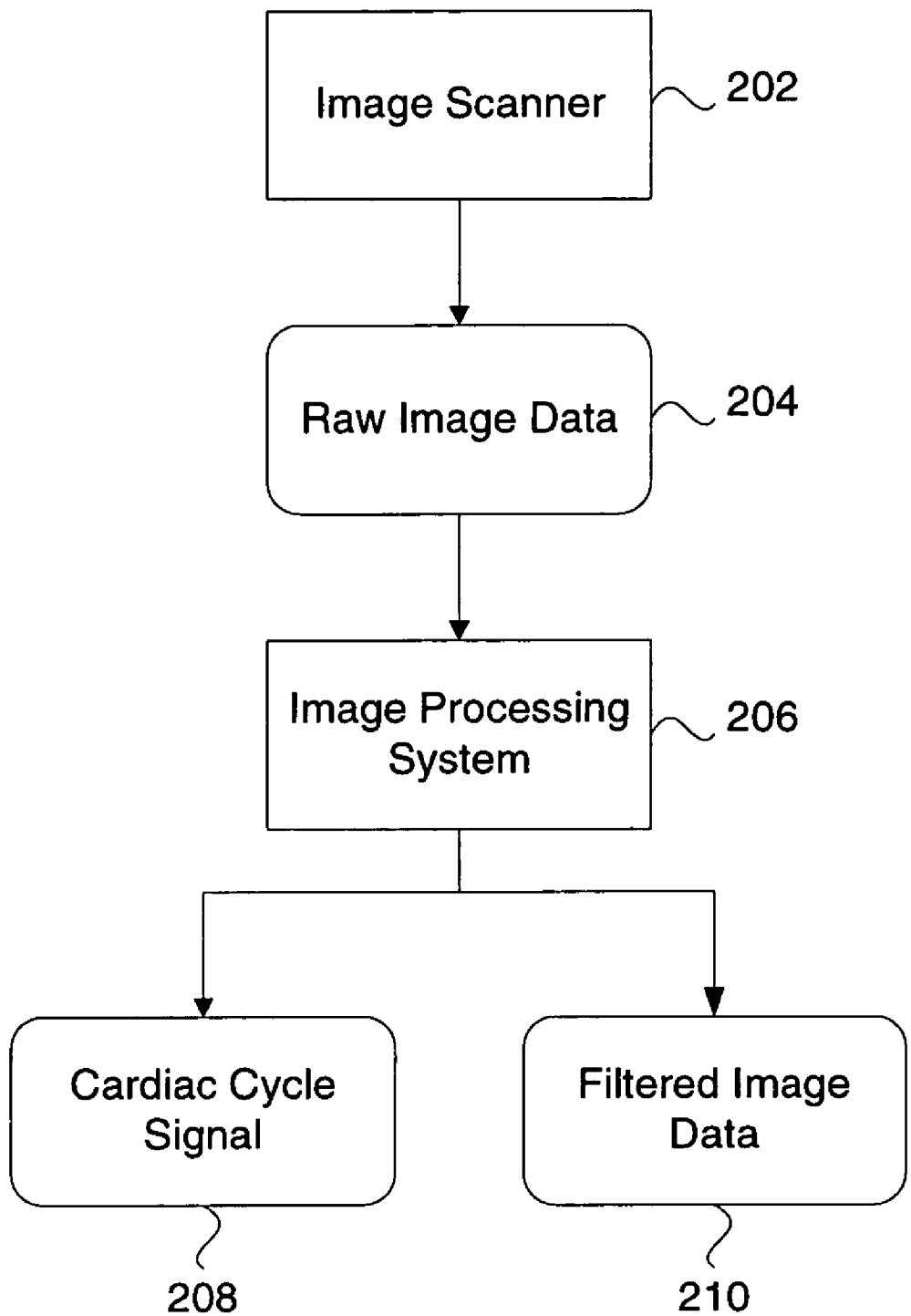
FIG. 2 is a diagram illustrating a system level overview of an exemplary embodiment of the invention.

The embodiments of the invention describe a software environment of systems and methods that provide for the retrospective gating of medical images. FIG. 2 is a block diagram describing the major components of such a system. As shown, the system includes an image scanner 202 and an image processing system 206.

Image scanner 202 in one embodiment of the invention is a CT scanner. The scanner can be a high-speed helical CT scanner, or it can be an electron beam CT scanner. However, the invention is not limited to CT scanners, an any scanner that can provide a sequence of images recorded over a period of time are within the scope of the invention. For example, scanner 202 could be a Magnetic Resonance Imaging (MRI) or ultrasound scanner.

Scanner 202 produces image data 204 that comprises a sequence of two-dimensional images of the human body. This image data is then sent to image processing system 206 for processing. In one embodiment of the invention, image processing system 206 is the ImageGate system from Vital Images, Inc. The image data can be transferred from scanner 202 to image processing system 204 using any data transmission means, including tape media, CD-ROM, floppy-disk, removable hard drive, and network means, including the Internet.

Image processing system 206 is a suitably configured computer, such as the computer illustrated in FIG. 1, and employs the methods detailed below to perform retrospective gating of the image data. The output of system 206 comprises cardiac cycle signal 208 and filtered image data 210. Filtered image data 210 comprises the image data that corresponds to images acquired at desired points in the cardiac cycle signal 208.

This section has described the various system components in a system that performs image based retrospective gating of cardiac images. As those of skill in the art will appreciate, the software can be written in any of a number of programming languages known in the art, including but not limited to C/C++, Visual Basic, Smalltalk, Pascal, Ada and similar programming languages. The invention is not limited to any particular programming language for implementation.

Methods of an Exemplary Embodiment of the Invention

In the previous section, a system level overview of the operation of an exemplary embodiment of the invention was described. In this section, the particular methods of various embodiments of the invention performed by an operating environment executing an exemplary embodiment are described by reference to a flowchart shown in FIGS. 3 and 4. The methods to be performed by the operating environment constitute computer programs made up of computer-executable instructions. Describing the methods by reference to a flowchart enables one skilled in the art to develop such programs including such instructions to carry out the methods on suitable computers (the processor of the computer executing the instructions from computer-readable media). The methods illustrated in FIGS. 3 and 4 are inclusive of the acts required to be taken by an operating environment executing an exemplary embodiment of the invention.

The methods of the various embodiments of the invention illustrated below operate to perform time categorization and selection of a subset of images from a plurality of images based on the image data alone, that is, without reference to any external signals such as an EKG. In some embodiments of the invention, the plurality of images comprise a series of images that are received from a CT scanning system in which multiple images are taken at different points in time of a single space of a body. In other embodiments, the plurality of images can comprise a sequence of images in which one image of a space of a body at a single point in time is taken.

Figure 3:
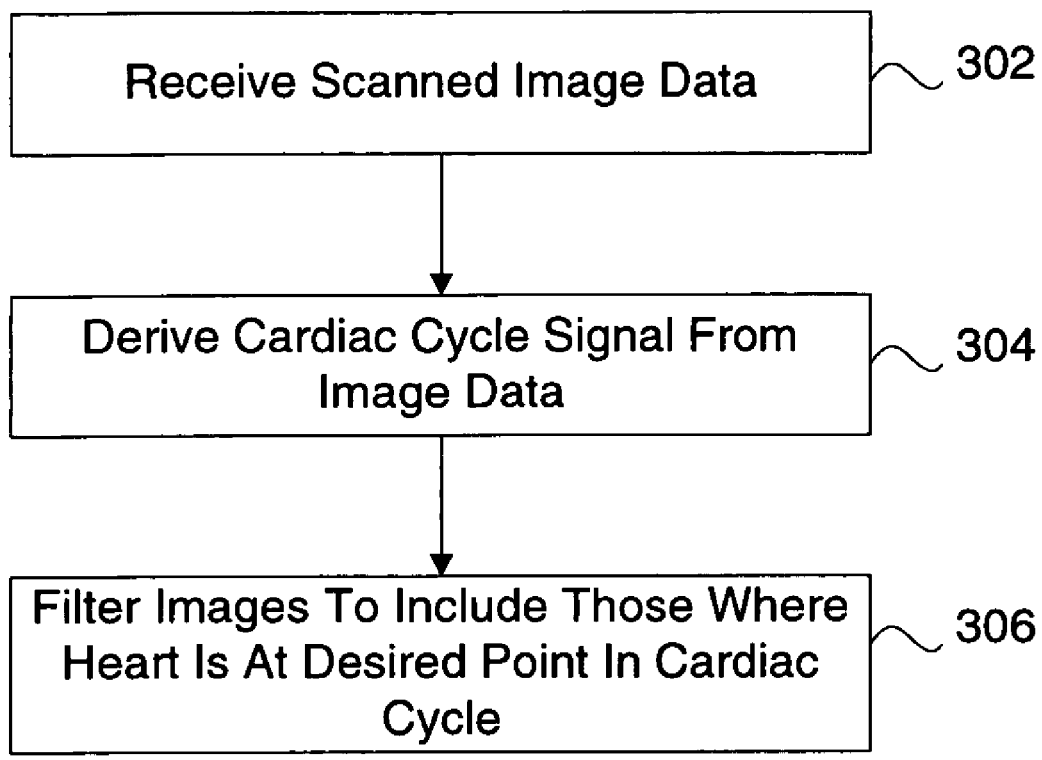
FIG. 3 is a flowchart illustrating a method for performing retrospective gating of medical image data according to an exemplary embodiment of the invention.
Figure 4:
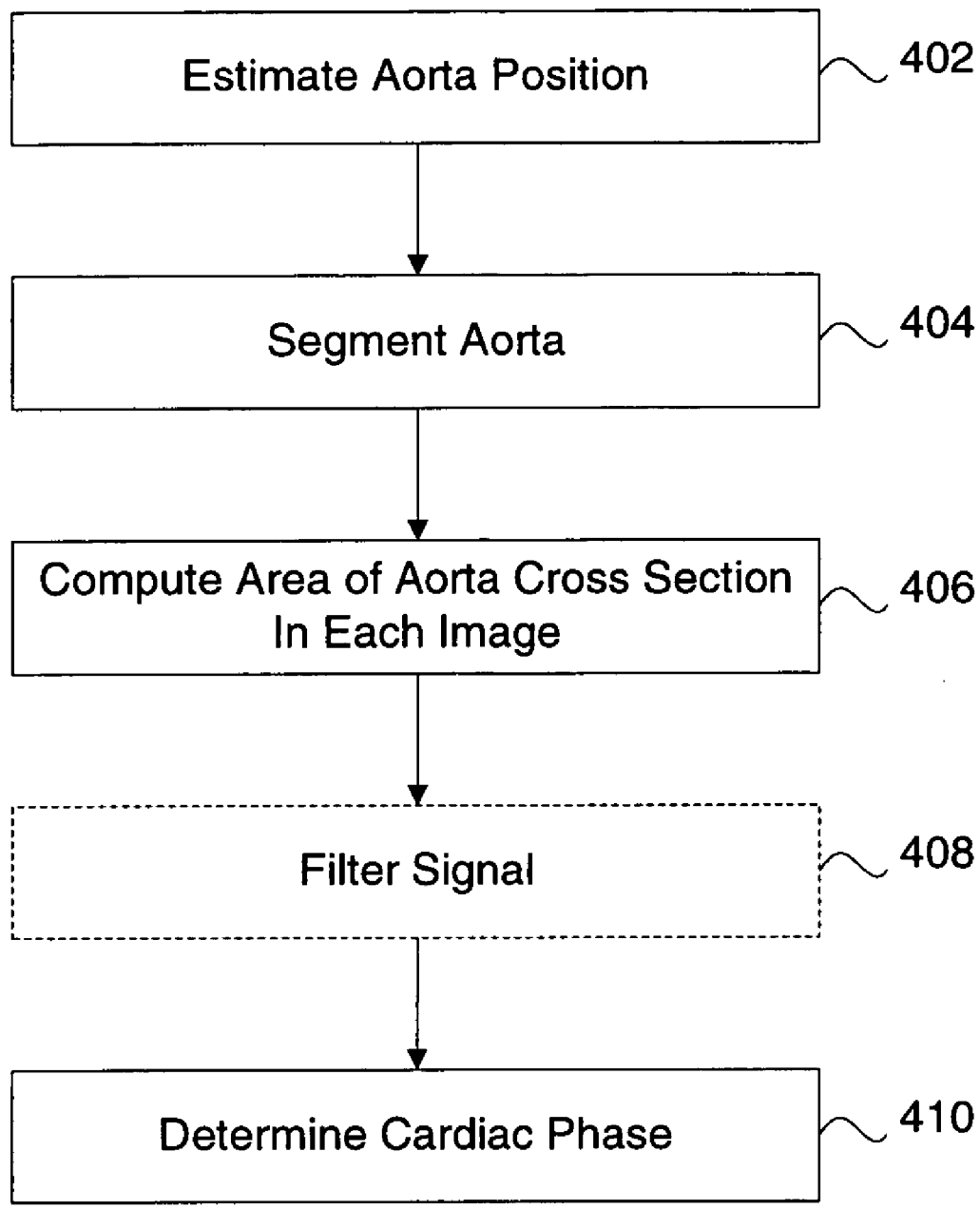
FIG. 4 is a flowchart providing further details on determining a signal used to filter images.

A method for categorizing and selecting images according to an embodiment of the invention for performing image-based retrospective gating of scanned medical image data is illustrated in FIG. 3. A system executing the method begins by receiving scanned image data (block 302). In one embodiment of the invention, the scanned image data is received from a CT scanner such as scanner 202 (FIG. 2). However, the invention is not limited to any particular method of obtaining the scanned image data. As will be appreciated by those of skill in the art, any system capable of producing a volumetric sequence of images is within the scope of the invention. It is desirable that the images are heavily overlapped axial images of the chest. The axial overlap provides the ability for the system to select a subset of images acquired when the heart was most at rest and still adequately sample the heart to its full anatomical extent.

In one embodiment of the invention, the categorization and selection of images operates to select those images that are the least blurred. In the case of cardiac image data, the least blurred images represent those points in time in the cardiac cycle when the heart is at rest in between beats. In some embodiments of the invention, a Fourier transform is used to determine "blurriness" of an image.

In alternative embodiments, the Mean Pixel Difference (MPD) between one image and a subsequent adjacent image is determined. The images with the lowest MPD are selected as being the least blurry images. In MPD, each pixel on a first axial image is subtracted from the corresponding pixel on the subsequent adjacent axial image. The absolute value of the pixel differences for the image are summed and divided by the number of pixels in the image. This single number for each image is the MPD. An image with a lower MPD than another image can be said to be less blurry.

Next, those images that are the least blurry, or whose blurriness are within a particular tolerance, are then selected for inclusion in the set of images for which further analysis, such as volumetric analysis, will be performed.

The image processing system derives a cardiac cycle signal from the image data (block 304). The various phases of the cardiac cycle can be derived from the image data by detecting in the image data the corresponding motion or changes of different parts of the heart and/or other parts of the body affected by the motion of the heart, such as blood vessels. By measuring this motion as a function of a time, a periodic signal can be derived that can be used to determine heart rate and cardiac cycle phase for any time during the image data collection.

Finally, the image data is filtered according to the cardiac cycle signal determined at block 304 to select those images that where acquired when the heart was most at rest (block 306). The filtered images can then be used to render accurate volumetric images of the heart.

Various methods can be used to determine the cardiac cycle in block 304 above. The methods generally determine the cycle based on criteria common to the images. One such method according to an embodiment of the invention detects changes in the cross-section of the aorta, and is illustrated in FIG. 4. The method begins by estimating the position of the aorta (block 402). Various means can be used to detect the position of the aorta. For example, in some embodiments of the invention, a matching filter as is known in the art is used to detect the aorta. In alternative embodiments, an Active Appearance Model is used to detect the position. In further alternative embodiments, an Active Shape Model is used.

In still further embodiments of the invention, an algorithm called Hough Transform is used to find the approximate aorta position. As is known in the art, the Hough Transform can be regarded as a generalized template matching method, and is typically used to extract out edges or curves from an image. The Hough Transform can be used to extract circles and even generalized (perhaps non-symmetrical) edges. Use of the Hough Transform is desirable, because it is invariant to rotation and translation. Further details on the Hough Transform can be found in U.S. Pat. No. 3,069,654, which is hereby incorporated by reference herein. For the purpose of Hough Transform, aorta can be described as a circle of radius in a range 8–25 mm.

In one embodiment of the invention, the position of the aorta is determined only in the first image. For the following images, the results of segmentation in the previous image are used. This is desirable because it reduces the time required to execute the method. The approximate aorta border in the (z+1) image is defined as a circle of radius Rres, where Rres is the radius of the circle found by Hough transform in image z. The circle is centered at position (Xc(z), Yc(z)), which is the center of aorta found in the previous, z image. Because processing each image is a sequential process, it is vulnerable to error propagation. In one embodiment of the invention, the likelihood of possible error propagation is reduced by using the same circle radius to initialize the aorta segmentation and only updating its position in subsequent images.

In another embodiment of the invention, a voting mechanism for detecting the aorta is used. The Hough Transform is applied to a sequence of five consecutive images. A result is accepted, if the aorta center is found in a similar location in at least four of these images. If such a match is not found, another set of five images is investigated.

In the Hough transform, a fit value is determined for every pixel in an image. The fit value represents the probability that the point belongs to the aorta border. The computation of fit values is based on a priori knowledge of the aorta properties in CT images.

For every pixel (x, y) in an image, the fit value is computed as $$fit(x, y) = \begin{cases} 0 & \text{if } I(x, y) < -100HU \text{ or } I(x, y) > 200HU \\ f[\vec{g}(x, y)\vec{n}_{expected}] & \text{otherwise} \end{cases} \quad (1)$$

where:

I(x, y) is the image intensity in Hounsfield Units [HU].

$\vec{g}$ is the image gradient.

$\vec{n}_{expected}$ is the expected direction of the gradient.

In one embodiment of the invention, a directional gradient detector based on 5×5 Gaussian mask is used. In the case of the Hough Transform, the expected direction is not known. Therefore, one embodiment of the invention uses the following formula to set $\vec{n}_{expected}$:

$$\vec{n}_{expected} = \frac{\vec{g}}{|\vec{g}|} \quad (2)$$

Function f(.) in formula (1) is a transformation function that limits the maximum value of the considered gradient. The transformation function f(.) in one embodiment of the invention is:

$$f(a) = \begin{cases} a : a < a_{MAX} \\ a_{MAX} : a \geq a_{MAX} \end{cases} \quad (3)$$

where $\alpha_{MAX}$ is the gradient response to a step edge of volume 100 HU.

After estimating the position of the aorta, the method then segments (i.e. detects) the aorta in each of the 2D images in the sequence (block 404). In some embodiments of the invention, edge-based dynamic programming as is known in the art is applied to the images in order to segment the aorta. In alternative embodiments, Active Contours, also referred to as "Snakes" are used to detect the aorta. In further embodiments of the invention, region growing algorithms are used to detect the aorta. Such algorithms are known in the art.

In one particular embodiment of the invention, the aorta is segmented using a dynamic programming based boundary detection algorithm. Details of such a boundary detection algorithm are presented in M. Sonka, V. Hlavac, R. Boyle, *Image Processing, Analysis, and Machine Vision*; PWS Publishing, $2^{nd}$ edition, 1998, pp. 158–163, which is hereby incorporated by reference herein. The approximate aorta location determined at block 402 is used to create a Region of Interest (ROI) within which the aorta boundary is sought. For the purpose of searching the image for the aorta, the ROI is mapped into a rectangular graph, in which every node $(X_G, Y_G)$ corresponds to one image pixel. This is expressed in the following formula:

$$(x_G, y_G) = centerlinePoint(x_G) + \vec{n}_c(x_G) \cdot \left(y_G - \frac{\text{width}}{2}\right) \quad (4)$$

where:

$\vec{n}_c$ is the unit normal vector to the circular centerline at $x_G$th point along the centerline; and width is the width of the ROI.

Every node in the rectangular graph has a cost associated with it. The cost is given by the formula:

$$cost(x, y) = \max_{i,j}(fit(i, j) - fit(x, y)) \quad (5)$$

where:

fit is defined by Equation 1 with $n_{expected} = n_c$.

The method finds a path of minimal cost between any node in the first column and any node in the last column of the rectangular graph. To ensure that the found boundary is a closed contour, the search is restricted by forcing the first and last points of the minimal cost path have to have the same $Y_G$ coordinate in the rectangular graph.

In addition to assigning a cost to every graph node, a cost is assigned to every link between graph nodes. Only nodes in 2 consecutive columns are connected by links. The costs are assigned according to the following formula:

$$\text{cost}[(x_i, y_j), (x_i + 1, y_k)] \begin{cases} 0 & \text{if } k = j \\ 0.3 \cdot \text{cost}(x_i, y_j) & \text{if } k = j \pm 1 \\ \infty & \text{otherwise} \end{cases} \quad (6)$$

Such a cost assignment effectively connects only nodes whose y coordinate differs by no more than one. It ensures connectivity of the resulting boundary. The middle rule in Equation 6 for assigning cost reflects the knowledge that the sought border should be circular. Thus, a border that is parallel to the ROI centerline (a circle) is considered to be a preferred direction over a direction that diverges from the ROI centerline direction. The minimum cost path is then mapped into the original image and represents the aorta border.

After determining the position of the aorta, the method then computes the area of the aorta cross-section in the image (block 406). The cross-sectional area in the image is then used to compute an approximation of the volume of aorta at the time of an image acquisition. The area is computed as an area enclosed by the aorta border found by the aorta segmentation in block 404. In one embodiment of the invention, for every image, the found border is projected onto a plane that is perpendicular to the aorta direction. This provides better approximation of the true cross-sectional area of the aorta in cases when the image acquisition plane is not perpendicular to the aorta direction.

The aorta direction for a given image can be approximated by a tangent to a line connecting centers of gravity of outlined aorta boundaries. In some embodiments of the invention, the line is smoothed using algorithms known in the art.

Every border point $(x, y, z)$ is projected into a point $(x_P, y_P, z_P)$ as follows:

$$\begin{bmatrix} x_P \\ y_P \\ z_P \end{bmatrix} = \begin{bmatrix} x \\ y \\ z \end{bmatrix} + \begin{bmatrix} \vec{t}_x \\ \vec{t}_y \\ \vec{t}_z \end{bmatrix} (\vec{t} \cdot \vec{c}) \quad (7)$$

where:
- $\vec{t}$ is the unit vector representing aorta direction; and
- $\vec{c}$ is a vector connecting the boundary point $(x, y, z)$ with the aorta center in the given image.

The aorta center can be computed from its boundary points, yielding the following computation of the vector $\vec{c}$:

$$\vec{c} = \begin{bmatrix} x \\ y \\ z \end{bmatrix} - \frac{1}{N_B} \sum_{i=1}^{N_B} \begin{bmatrix} x_i \\ y_i \\ z_i \end{bmatrix} \quad (8)$$

where:
$(x_i, y_i, z_i)$ are the aorta boundary points
$N_B$ is the total number of boundary points.

In some embodiments of the invention, the area computation is simplified by expressing the projected border in a new coordinate system $(w_x, w_y, w_z)$ in which the $w_z$ coordinate of all the boundary points is zero. The new coordinate system is determined as follows:

$$\begin{bmatrix} \vec{w}_z \\ \vec{w}_y \\ \vec{w}_x \end{bmatrix} = \begin{bmatrix} \vec{t} \\ \frac{\vec{e}_y - \vec{w}_z \cdot (\vec{w}_z \cdot \vec{e}_y)}{|\vec{e}_y - \vec{w}_z \cdot (\vec{w}_z \cdot \vec{e}_y)|} \\ \frac{\vec{e}_x - \vec{w}_z \cdot (\vec{w}_z \cdot \vec{e}_x) - \vec{w}_y \cdot (\vec{w}_y \cdot \vec{e}_x)}{|\vec{e}_x - \vec{w}_z \cdot (\vec{w}_z \cdot \vec{e}_x) - \vec{w}_y \cdot (\vec{w}_y \cdot \vec{e}_x)|} \end{bmatrix} \quad (9)$$

Thus, the coordinate transformation can be computed as:

$$\begin{bmatrix} x' \\ y' \\ z' \end{bmatrix} = T \begin{bmatrix} x_P \\ y_P \\ z_P \end{bmatrix} \quad (10)$$

where:

$$T = \begin{bmatrix} \vec{w}_x \cdot x & \vec{w}_x \cdot y & \vec{w}_x \cdot z \\ \vec{w}_y \cdot x & \vec{w}_y \cdot y & \vec{w}_y \cdot z \\ \vec{w}_z \cdot x & \vec{w}_z \cdot y & \vec{w}_z \cdot z \end{bmatrix} \quad (11)$$

Because $z'=0$ for all points of the transformed border, in some embodiments the area of the aorta cross-section is computed using a discrete implementation of Simpson's Rule. Such algorithms are known in the art.

The sequence of values representing the aorta cross-sectional areas represent an in-time regularly sampled signal that can be used to compute the heart rate and the phase of the cardiac sample for every image in the sequence.

In some embodiments of the invention, the signal determined is filtered to remove noise and to simplify cardiac phase determination (block 408). In some embodiments of the invention, filtering is performed by a Butterworth filter. It is desirable that the filter is designed so that there is no more than 3dB attenuation in the pass band and at least 40dB attenuation in the stop band. In order to determine the band pass of the filter, the aorta area signal is first High Pass Filtered (HPF) in order to remove DC component and low frequencies that may correspond to the change of aorta size in space rather than in time. In some embodiments, the HPF signal ($S_{HPF}$) is computed using a digital high-pass filter based on the Butterworth filter.

Next, the heart rate is determined. In some embodiments, it is estimated by determining the main frequency component in the area signal. It is desirable to avoid rasterization and to ensure stability, thus some embodiments determine the main frequency not from the original signal, but from the signal's autocorrelation:

$$f_{MAX} = \arg\max\|\text{Fourier}\{sHPF * sHPF\}\| \quad (12)$$

where * denotes the correlation operation.

The raw aorta area signal is then filtered with a Butterworth filter with a passing band of $<0.7f, 1.3f>$, which represents an estimated variation of the heart rate for a single patient during the scanning procedure. In order to improve the filtering results, some embodiments use the signal obtained using the above-described filtering to compute new values of $f_L$ and $f_H$. The beginning of each period is determined by positively sloped zero crossings of the signal.

The newly obtained limits are used to finally filter the signal according to the following formula:

$$S^{BPF}(x) = \text{Butterworth}\{s(x), f_L, f_H\},$$

where:
s denotes the raw aorta area signal; and $<f_L, f_H>$ is the frequency range of the pass band. (13)

In alternative embodiments, signal filtering is performed by applying an alternative HPF to the aorta signal, again, in order to remove DC component and low frequencies that may correspond to change of aorta size in space rather than in time. In these embodiments, the HPF can be approximated by subtracting a moving average from the original signal according to the following:

$$S^{HPF}(x) = s(x) - \sum_{i=-7}^{7} s(x+i) \quad (14)$$

where s denotes the raw aorta area signal.

Next, in order to remove noise from the signal and thus simplify the determination of points of maximum positive gradient that corresponds to the opening of aortic valve, the signal is smoothed.

In alternative embodiments of the invention, smoothing is performed using Band Pass Filtering (BPF) in a frequency domain. A moving window Fourier Transform can be used to smooth the signal separately in short segments. The window width is chosen so that it corresponds to approximately three cardiac cycles and is a power of 2 (to simplify the employment of Fast Fourier Transform algorithm). The width of the BPF is chosen to be one, thus considering only the basic frequency that occurs in the given segment of the signal. The BPF frequency is selected as the highest frequency in the spectrum (not considering zero frequency—the signal offset). The window for the Fourier Transform is always moved by just one sample and the smoothed signals are averaged in the time domain. The filtering is illustrated in the following formula:

$$BPF_i(s_{<i,i+w>}) = \text{Fourier}^{-1}\{\text{Fourier}\{s_{<i,i+w>}\} \cdot \text{Filter}_{f_i}\} \quad (15)$$

where:
Filter is a BPF with a passing frequency:

$$fi = \arg \max_{f \in <1, w/2>} \text{Fourier}\{s_{<i,i+w>}\} \quad (16)$$

and the window width w is a power of 2.
The final filter signal is thus:

$$S^{BPF}(i) = \sum_{j=\max(i-w,0)}^{\min(i,N-w)} BPF(S_{<j,j+w>})(i-j) \frac{1}{\min(i, N-w) - \max(i-w, 0)} \quad (17)$$

where N is the number of samples in the aorta area signal.

After the signal has been filtered, the method determines the cardiac phase (block 410). Depending on the heart rate of the person being scanned and on the image acquisition speed, 6–12 images can typically be obtained per cardiac cycle. It is generally the case that the opening of the aortic valve is followed by the maximum rate of change (max. gradient) of aortic pressure that is reflected by the maximum gradient of increase of aorta cross-sectional area. This happens approximately 0.1 seconds after the beginning of ventricular polarization. To match the aorta area signal to the heart cycle the method searches for the points of maximum positive gradient, which generally correspond to the moments of aortic valve opening.

The filtered signal approximates the time change of aorta cross-sectional area (volume) during a cardiac cycle. Thus, one period of the signal corresponds to one cardiac cycle. Since signal can be approximated by a sine wave, the maximum positive derivative of the signal can be determined and used as the point of a positively sloped zero crossing. Using linear interpolation, the method can determine that the zero crossing point $x_z$ between signal points (x, $y_1$) and (x+1, $y_2$), such that is:

$$x_z = \frac{y_1}{y_1 - y_2} + x \quad (18)$$

Thus the set of times ($x_z$) represents the instants corresponding to aortic valve openings. From the aortic valve openings, the point in the cardiac cycle signal can be determined where the heart is most at rest.

In order to remove possible errors in the signal filtering, some embodiments of the invention perform post-processing on the signal. Based on the derived heart rate statistics (mean and standard deviation), outliers representing too short heart rate can be removed and/or a heart cycle can be added if the measured one is too long.

The above-described signal filtering techniques can be used for both helical scanning systems and for multi-slice scanning systems. In the case of multi-slice scanning systems, the scanning protocol is generally a "step and shoot" procedure, which results in a signal consisting of short measured pieces (1–2 heart cycles) interlaced with segments of 1–2 heart cycles without any data. In such systems there are typically more than one measurement of every segment. Usually there are four segments, and the segments are synchronized. In order to use the same filtering scheme as above, the existing signals are averaged to obtain one signal, resulting in a higher S/N ratio. Then, the missing segments of the signal are reconstructed. A method for restoration of lost samples in digital signals is described in detail in Raymond Veldhuis: *Restoration of Lost Samples in Digital Signals*. Prentice Hall International Series in Acoustics, Speech and Signal Processing, 1990 Prentice Hall International (UK) Ltd., ISBN-0-13-775198-2, Chapter 3 Autoregressive processes, pp. 28–56. In some embodiments, this algorithm is used to fill the missing data. However, the invention is not limited to the algorithm described in Veldhuis, and any algorithm capable of restoring lost samples can be used. When the signal is reconstructed to its full length, the same filtering scheme as described above can be employed.

The method of determining the cardiac cycle illustrated in FIG. 4 is desirable, for several reasons. First, it is easy to measure accurately because a reliable segmentation algorithm exists. Second, measuring the cross section of the aorta is insensitive to the shifting and twisting that occurs as the heart beats. Finally, measuring the cross section of the aorta is independent of heart geometry changes in the space domain (changes from one acquired image to another). However, the invention is not limited to deriving a cardiac cycle signal based on the changes in the area of the cross section of the aorta. For example, changes in the area of cross section of other blood vessels besides the aorta can be detected and used to derive a signal. In addition, the invention is not limited to detecting changes in the area of a blood vessel such as the aorta. In alternative embodiments of the invention, the motion of a blood vessel wall is determined and used to derive a signal.

Figure 5:
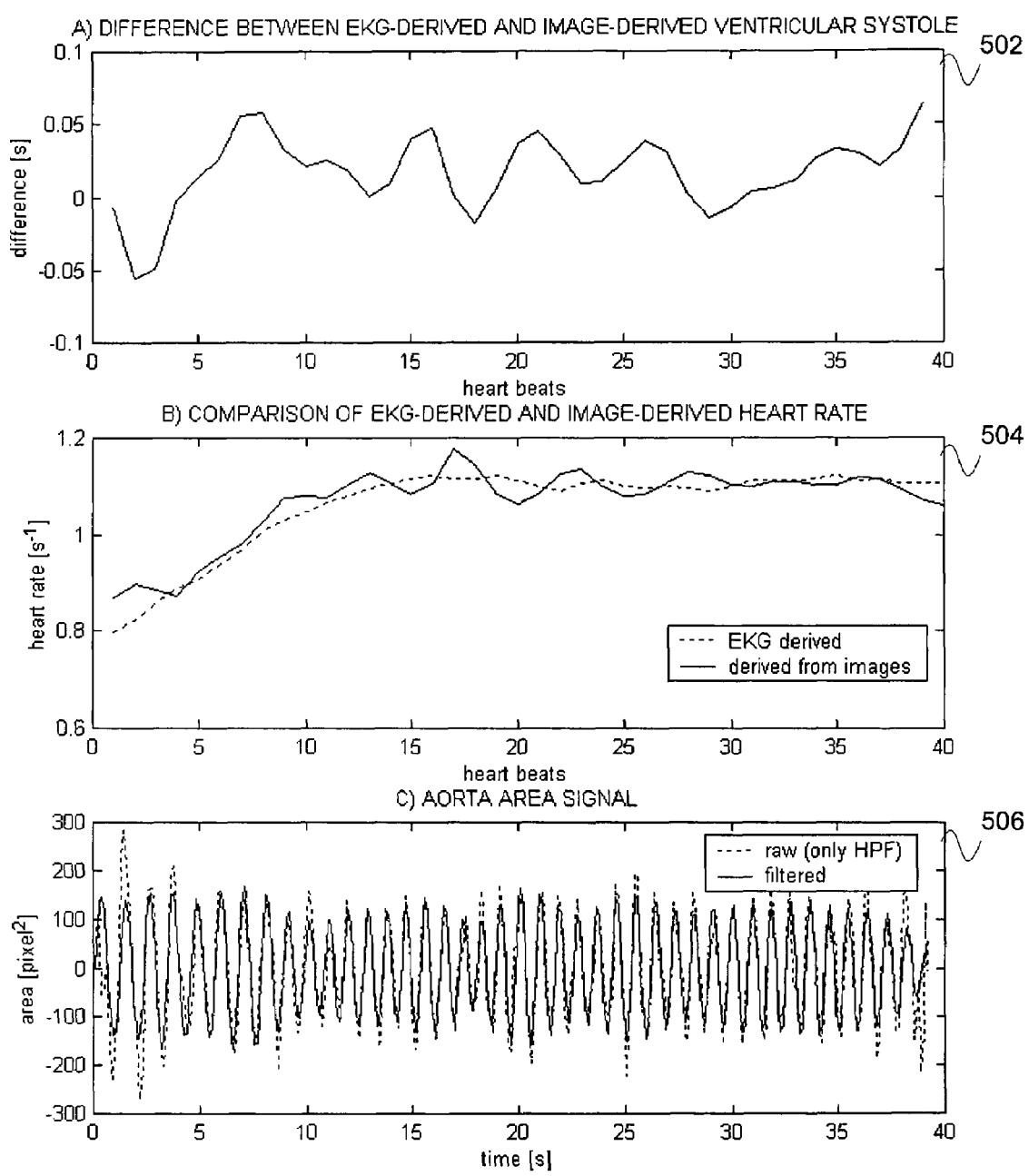
FIG. 5 provides a graph comparing the image based retrospective gating to prior art EKG gating.

FIG. 5 illustrates a sample of the signals obtained using the methods described above. Graph 502 illustrates the difference between an EKG-derived signal an image-derived signal for ventricular systole. Graph 504 illustrates the difference between an EKG-derived heart rate and an image-derived heart rate. Graph 506 presents two signals, a raw signal illustrated as a dashed line which represents the signal before filtering, and a filtered signal illustrated as a solid line which represents the signal after the filtering described above has applied.

In an alternative embodiment of the invention, the cardiac signal can be derived using a "Mean Pixel Difference" (MPD) between the acquired images. As noted above, in MPD, each pixel on a first axial image is subtracted from the corresponding pixel on the subsequent adjacent axial image. The absolute value of the pixel differences for the image are summed and divided by the number of pixels in the image. This single number for each image is the MPD.

The MPD thus represents a direct measure of changes in the data between two image slices. The sequence of MPD values can thus be used to derive a cardiac cycle signal. Using the MPD is not as desirable as using the changes in the area of cross-sections of the aorta, because other factors besides heart motion can affect the calculation of the MPD. For example, the difference is often caused not only by the heart motion, but also by the change of the heart geometry as the scan progresses both in the time and spatial domains.

In a further alternative embodiment of the invention, the cardiac signal can be derived using the fact that the heart volume periodically decreases and increases during systole and diastole. By measuring these changes in heart volume (or area of heart cross-section) across a sequence of images, a cardiac cycle can be computed. The reliable measurement of the heart cross-sectional area requires accurate segmentation of the heart in each of the images. The cross-sectional area can then be used to determine a cardiac cycle signal in a manner similar to that described above in reference to FIG. 4.

In a still further embodiment of the invention, heart border motion can be used to derive a cardiac cycle signal. Here, heart border motion is measured by detecting the motion in the walls of the heart. For example, the atrium and ventricle borders. This can provide the same information as measurement of heart cross-sectional area. In this embodiment, easy-to-segment parts of the heart are measured and the changes in the measurements used to derive a cardiac cycle signal.

CONCLUSION

Systems and methods for using image data to derive signals, such as cardiac cycle signals have been disclosed. The embodiments of the invention provide advantages over previous systems. For example, there is no need to attach wires to the patient for EKG, which can reduce patient apprehension and nervousness about the imaging procedure. Furthermore, deriving the cardiac cycle from the image data eliminates the possibility that the EKG cycle data does not match the image data due to mishandling of the EKG data, since no EKG data is required. Moreover, EKG data can provide a less than accurate cardiac cycle due to variations in the measurement of electrical signals generated by the heart. The image data captures the heart motion directly, unlike the EKG.

Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations of the present invention.

The terminology used in this application is meant to include all of these environments. It is to be understood that the above description is intended to be illustrative, and not restrictive. Many other embodiments will be apparent to those of skill in the art upon reviewing the above description. Therefore, it is manifestly intended that this invention be limited only by the following claims and equivalents thereof.

We claim:

1. A method for ordering a plurality of images of a portion of a cardiovascular system comprising:
   receiving from an image scanner a plurality of images recorded over a period of time, the images representing one or more locations along the extent of the cardiovascular system;
   deriving a cardiac cycle signal from the plurality of scanned images; and
   assigning a phase in the cardiac cycle to each scanned image,
   wherein deriving the cardiac signal comprises:
      segmenting a set of data representing a blood vessel in each image;
      computing a change value for the blood vessel; and
      determining the cardiac cycle signal based on a sequence of the change values for each image.

2. The method of claim 1, wherein the change value is a change in the area of a cross section of the blood vessel.

3. The method of claim 1, wherein the change value is a change in the position of a wall of the blood vessel.

4. A method for ordering a plurality of images of a portion of a cardiovascular system comprising:
   receiving from an image scanner a plurality of images recorded over a period of time, the images representing one or more locations along the extent of the cardiovascular system;
   deriving a cardiac cycle signal from the plurality of scanned images; and
   assigning a phase in the cardiac cycle to each scanned image,
   wherein deriving the cardiac cycle signal comprises:
      segmenting a set of data representing a cross-section of the aorta in each image;
      computing an area value representing an area of the cross-section; and
      determining the cardiac cycle signal based on a sequence of the area values for each image.

5. The method of claim 4, further comprising estimating the position of the aorta within the image data prior to segmenting the set of data.

6. The method of claim 5, wherein estimating the position of the aorta utilizes a Hough transform.

7. The method of claim 4, wherein segmenting of the aorta cross-section utilizes Dynamic Programming.

8. The method of claim 4, further comprising filtering the cardiac cycle signal to produce a smoothed cardiac cycle signal.

9. A method for ordering a plurality of images of a portion of a cardiovascular system comprising:
receiving from an image scanner a plurality of images recorded over a period of time, the images representing one or more locations along the extent of the cardiovascular system;
deriving a cardiac cycle signal from the plurality of scanned images; and
assigning a phase in the cardiac cycle to each scanned image,
wherein deriving the cardiac cycle signal comprises:
for each image in the plurality of images performing the tasks of:
selecting an adjacent subsequent image;
calculating a mean pixel difference between the image and the subsequent image; and
determining the cardiac cycle signal based on the mean pixel differences of the images.

10. A method for ordering a plurality of images of a portion of a cardiovascular system comprising:
receiving from an image scanner a plurality of images recorded over a period of time, the images representing one or more locations along the extent of the cardiovascular system;
deriving a cardiac cycle signal from the plurality of scanned images; and
assigning a phase in the cardiac cycle to each scanned image,
wherein deriving the cardiac cycle signal comprises:
segmenting a set of data representing a cross-section of a heart in each image;
computing an area value representing an area of the cross-section; and
determining the cardiac cycle signal based on a sequence of the area values for each image.

11. A method for ordering a plurality of images of a portion of a cardiovascular system comprising:
receiving from an image scanner a plurality of images recorded over a period of time, the images representing one or more locations along the extent of the cardiovascular system;
deriving a cardiac cycle signal from the plurality of scanned images; and
assigning a phase in the cardiac cycle to each scanned image,
wherein deriving the cardiac cycle signal comprises:
for each image in the plurality of images performing the tasks of:
determining a first border of a heart in the image;
determining a second border of the heart in a subsequent adjacent image;
determining the difference between the first border and the second border; and
determining the cardiac cycle based on a sequence of the differences.

12. A method for ordering a plurality of images of a portion of a cardiovascular system comprising:
receiving from an image scanner a plurality of images recorded over a period of time, the images representing one or more locations along the extent of the cardiovascular system;
deriving a cardiac cycle signal from the plurality of scanned images; and
assigning a phase in the cardiac cycle to each scanned image to produce an ordered set of images, wherein the ordered set of images is further filtered to produce a subset of images, said subset of images comprising images acquired at a desired point in the cardiac cycle signal.

13. A method for ordering a plurality of images of a portion of a cardiovascular system comprising:
receiving from an image scanner a plurality of images recorded over a period of time, the images representing one or more locations along the extent of the cardiovascular system;
deriving a cardiac cycle signal from the plurality of scanned images; and
assigning a phase in the cardiac cycle to each scanned image,
wherein the derived cardiac cycle signal is used to interpolate or reconstruct new images at specific phases in the cardiac cycle from the original scanned images or other related data.

14. A computer-readable medium having computer executable instructions for performing a method for ordering a plurality of images of a portion of a cardiovascular system, the method comprising:
receiving from an image scanner a plurality of images recorded over a period of time, the images representing one or more locations along the extent of the cardiovascular system;
deriving a cardiac cycle signal from the plurality of scanned images; and
assigning a phase in the cardiac cycle to each scanned image,
wherein deriving the cardiac signal comprises:
segmenting a set of data representing a blood vessel in each image;
computing a change value for the blood vessel; and
determining the cardiac cycle signal based on a sequence of the change values for each image.

15. The computer-readable medium of claim 14, wherein the change value is a change in the area of a cross section of the blood vessel.

16. The computer-readable medium of claim 14, wherein the change value is a change in the position of a wall of the blood vessel.

17. A computer-readable medium having computer executable instructions for performing a method for ordering a plurality of images of a portion of a cardiovascular system, the method comprising:
receiving from an image scanner a plurality of images recorded over a period of time, the images representing one or more locations along the extent of the cardiovascular system;
deriving a cardiac cycle signal from the plurality of scanned images; and
assigning a phase in the cardiac cycle to each scanned image,
wherein deriving the cardiac cycle signal comprises:
segmenting a set of data representing a cross-section of the aorta in each image;
computing an area value representing an area of the cross-section; and
determining the cardiac cycle signal based on a sequence of the area values for each image.

18. The computer-readable medium of claim 17, further comprising estimating the position of the aorta within the image data prior to segmenting the set of data.

19. The computer-readable medium of claim 18, wherein estimating the position of the aorta utilizes a Hough transform.

20. The computer-readable medium of claim 17, wherein segmenting of the aorta cross-section utilizes Dynamic Programming.

21. The computer-readable medium of claim 17, further comprising filtering the cardiac cycle signal to produce a smoothed cardiac cycle signal.

22. A computer-readable medium having computer executable instructions for performing a method for ordering a plurality of images of a portion of a cardiovascular system, the method comprising:
- receiving from an image scanner a plurality of images recorded over a period of time, the images representing one or more locations along the extent of the cardiovascular system;
- deriving a cardiac cycle signal from the plurality of scanned images; and
- assigning a phase in the cardiac cycle to each scanned image,
- wherein deriving the cardiac cycle signal comprises:
  - for each image in the plurality of images performing the tasks of:
    - selecting an adjacent subsequent image;
    - calculating a mean pixel difference between the image and the subsequent image; and
    - determining the cardiac cycle signal based on the mean pixel differences of the images.

23. A computer-readable medium having computer executable instructions for performing a method for ordering a plurality of images of a portion of a cardiovascular system, the method comprising:
- receiving from an image scanner a plurality of images recorded over a period of time, the images representing one or more locations along the extent of the cardiovascular system;
- deriving a cardiac cycle signal from the plurality of scanned images; and
- assigning a phase in the cardiac cycle to each scanned image,
- wherein deriving the cardiac cycle signal comprises:
  - segmenting a set of data representing a cross-section of a heart in each image;
  - computing an area value representing an area of the cross-section; and
  - determining the cardiac cycle signal based on a sequence of the area values for each image.

24. A computer-readable medium having computer executable instructions for performing a method for ordering a plurality of images of a portion of a cardiovascular system, the method comprising:
- receiving from an image scanner a plurality of images recorded over a period of time, the images representing one or more locations along the extent of the cardiovascular system;
- deriving a cardiac cycle signal from the plurality of scanned images; and
- assigning a phase in the cardiac cycle to each scanned image,
- wherein deriving the cardiac cycle signal comprises:
  - for each image in the plurality of images performing the tasks of:
    - determining a first border of a heart in the image;
    - determining a second border of the heart in a subsequent adjacent image;
    - determining the difference between the first border and the second border; and
    - determining the cardiac cycle based on a sequence of the differences.

25. A computer-readable medium having computer executable instructions for performing a method for ordering a plurality of images of a portion of a cardiovascular system, the method comprising:
- receiving from an image scanner a plurality of images recorded over a period of time, the images representing one or more locations along the extent of the cardiovascular system;
- deriving a cardiac cycle signal from the plurality of scanned images; and
- assigning a phase in the cardiac cycle to each scanned image to produce an ordered set of images, wherein the ordered set of images is further filtered to produce a subset of images, said subset of images comprising images acquired at a desired point in the cardiac cycle signal.

26. A computer-readable medium having computer executable instructions for performing a method for ordering a plurality of images of a portion of a cardiovascular system, the method comprising:
- receiving from an image scanner a plurality of images recorded over a period of time, the images representing one or more locations along the extent of the cardiovascular system;
- deriving a cardiac cycle signal from the plurality of scanned images; and
- assigning a phase in the cardiac cycle to each scanned image,
- wherein the derived cardiac cycle signal is used to interpolate or reconstruct new images at specific phases in the cardiac cycle from the original scanned images or other related data.

* * * * *

UNITED STATES PATENT AND TRADEMARK OFFICE
CERTIFICATE OF CORRECTION

| | | |
|---|---|---|
| PATENT NO. | : 7,031,504 B1 | |
| APPLICATION NO. | : 09/669395 | |
| DATED | : April 18, 2006 | |
| INVENTOR(S) | : Argiro et al. | |

It is certified that error appears in the above-identified patent and that said Letters Patent is hereby corrected as shown below:

On title page, (item (56)), under "Other Publications", in column 2, line 1, delete "Clos" and insert - - Cios - -, therefor.

column 13, line 17, after "has" insert - - been - -.

Signed and Sealed this

Fifteenth Day of August, 2006

JON W. DUDAS
*Director of the United States Patent and Trademark Office*